(12) United States Patent
Sun et al.

(10) Patent No.: US 11,124,890 B2
(45) Date of Patent: Sep. 21, 2021

(54) METHOD FOR MEASURING CONCENTRATIONS OF METAL ION IN ELECTRODEPOSITION SOLUTIONS

(71) Applicant: Hong Kong Applied Science and Technology Research Institute Company Limited, Hong Kong (CN)

(72) Inventors: Yaofeng Sun, Hong Kong (CN); Shaoqin Xie, Shenzhen (CN); Liya Zheng, Hong Kong (CN)

(73) Assignee: Hong Kong Applied Science and Technology Research Institute Company Limited, Hong Kong (CN)

( * ) Notice: Subject to any disclaimer, the term of this patent is extended or adjusted under 35 U.S.C. 154(b) by 324 days.

(21) Appl. No.: 16/398,339

(22) Filed: Apr. 30, 2019

(65) Prior Publication Data
US 2020/0347510 A1    Nov. 5, 2020

(51) Int. Cl.
C25D 21/14    (2006.01)
G01N 27/42    (2006.01)
G01N 33/208   (2019.01)

(52) U.S. Cl.
CPC .............. *C25D 21/14* (2013.01); *G01N 27/42* (2013.01); *G01N 33/208* (2019.01)

(58) Field of Classification Search
CPC .... G01N 33/208; G01N 27/42; G01N 27/423; C25D 21/12; C25D 21/14
See application file for complete search history.

(56) References Cited

U.S. PATENT DOCUMENTS

| | | | | |
|---|---|---|---|---|
| 5,174,886 | A | * | 12/1992 | King .................... C25D 3/38 205/125 |
| 6,527,920 | B1 | * | 3/2003 | Mayer ................... C25D 21/12 204/237 |
| 6,673,226 | B1 | | 1/2004 | Kogan et al. |
| 9,075,941 | B2 | | 7/2015 | Sun et al. |
| 2003/0062266 | A1 | | 4/2003 | Chalyt et al. |
| 2003/0183539 | A1 | | 10/2003 | Los et al. |
| 2005/0236280 | A1 | | 10/2005 | Han et al. |

FOREIGN PATENT DOCUMENTS

| | | |
|---|---|---|
| CN | 1912610 B | 11/2011 |
| CN | 104569122 B | 5/2017 |

OTHER PUBLICATIONS

See et al., "Effect of Concentration on the Electrochemistry and Speciation of the Magnesium Aluminum Chloride Complex Electrolyte Solution," ACS Appl. Mater. Interfaces 2017, 9, 35729-35739 with Supporting Information (Year: 2017).*

N. M. Hashemian, B. G. Lipták. Oct. 6, 2016, Calibration from : vol. I Measurement and Safety, Instrument and Automation Engineers' Handbook CRC Press (Year: 2016).*

(Continued)

*Primary Examiner* — Alexander S Noguerola
(74) *Attorney, Agent, or Firm* — Spruson & Ferguson (Hong Kong) Limited

(57) ABSTRACT

Provided herein is a method for measuring a concentration of a metal ion in an electrodeposition solution. The method of the present disclosure can substantially reduce the interference of organic additives and different electrode conditions on voltammetric metal ion concentration measurements.

20 Claims, 6 Drawing Sheets

(56) References Cited

OTHER PUBLICATIONS

W. John Eilbeck, J. Chem. Educ. 1980, 57, 11, 834 (Year: 1980).*
Haak et al., Cyclic Voltammetric Stripping Analysis of Acid Copper Sulfate Plating Baths—Part 2: Sulfoniumalkanesulfonate-Based Additives, Plat and Surf.Fin. 69, (3), 62 (1982) (Year: 1982).*
"A Guide to Acids, Acid Strength, and Concentration," © Compound Interest 2016 (hereafter "Compound Interest"), one page, no author indicated (Year: 2016).*
Compound summary for copper sulfate pentahydrate on NIH—National Library of Medicine website https://pubchem.ncbi.nlm.nih.gov/compound/Copper-sulfate-pentahydrate; downloaded May 17, 2021 (Year: 2021).*
Wikipedia "copper" entry; downloaded May 17, 2021 (Year: 2021).*

\* cited by examiner

METHOD FOR MEASURING CONCENTRATIONS OF METAL ION IN ELECTRODEPOSITION SOLUTIONS

TECHNICAL FIELD

The present disclosure generally relates to a method for measuring a concentration of a metal ion in an electrodeposition solution.

BACKGROUND

Electrodeposition solutions typically contain a metal ion, an acid, chloride ion and organic additives for electrodeposition (e.g., a suppressor, accelerator and leveler). In order to obtain satisfactory deposition of a metal, the concentrations of a metal ion and organic additives in an electrodeposition solution should be accurately monitored and controlled.

For example, during integrated circuit fabrication, if the concentrations of the chemical components of a plating bath are not carefully monitored and controlled, the deposited interconnects cannot meet the quality requirement, which may result in failure of integrated circuit.

Cyclic voltammetric stripping (CVS) analysis is commonly used for determining concentrations of organic additives in electroplating baths. The suppressor, accelerator, and leveler concentrations are measured using CVS analysis based on their effects exerted on metal electrodeposition rates. However, different initial electrode conditions (e.g., different potential differences) and varied electrolyte temperature may affect accuracy of the measurement of organic additive concentrations.

For measuring concentrations of a metal ion in electroplating baths, iodometric titration and inductively coupled plasma mass spectrometry are commonly used. However, iodometric titration is time-consuming and requires reagents, and the inductively coupled plasma mass spectrometry is expensive and requires skilled staff to operate. Additionally, both of iodometric titration and inductively coupled plasma mass spectrometry can measure the concentration of metal ions only. Thus, two measurement setups are required for measuring metal ion concentrations and organic additive concentrations in an electrodeposition solution respectively, which substantially increases operation costs.

A need therefore exists for an improved method for analyzing the chemical components of electrodeposition solutions that eliminates or at least diminishes the disadvantages and problems described above.

SUMMARY

Provided herein is a method for measuring a concentration ($C_u$) of a metal ion in an electrodeposition solution comprising the steps of: providing a supporting electrolyte solution, wherein the supporting electrolyte solution is acidic and has a concentration of chloride ion less than 0.05 ppm; providing a slope ($S_c$) of a first linear relationship characterizing electrodeposition rates at different concentrations of the metal ion in a calibration mixture; providing a plurality of samples of a test mixture, wherein each sample of the test mixture is prepared by contacting a supporting volume ($V_o$) of the supporting electrolyte solution with a respective addition volume of the electrodeposition solution, and the respective addition volumes used in preparing the plurality of samples of the test mixture are different; measuring an electrodeposition rate for each sample of the test mixture using a voltammetric measurement method; calculating a slope ($S_s$) of a second linear relationship characterizing electrodeposition rates at different addition volumes of the electrodeposition solution in the test mixture based on the measured electrodeposition rates of the plurality of samples of the test mixture and the respective addition volumes of the plurality of samples of the test mixture; and calculating the concentration of the metal ion in the electrodeposition solution by the following equation:

$$c_u = \frac{S_s}{S_c} \cdot V_0.$$

In certain embodiments, the electrodeposition solution comprises the metal ion, an acid, chloride ion, and one or more organic additives for electrodeposition.

In certain embodiments, the electrodeposition solution has a concentration of the chloride ion between 20 ppm and 100 ppm.

In certain embodiments, the supporting electrolyte solution has a pH value less than 2.

In certain embodiments, each sample of the test mixture has a volume ratio of the supporting volume of the supporting electrolyte solution to the respective addition volume of the electrodeposition solution being between 100:1 and 10000:1.

In certain embodiments, the calibration mixture comprises the same chemical components of the test mixture.

In certain embodiments, the voltammetric measurement method is a cyclic voltammetric scanning method, a cyclic pulse voltammetric scanning method, a chronoamperometric method, or a chronopotentiometric method.

In certain embodiments, the step of providing a plurality of samples of a test mixture comprises the steps of: (A) contacting a first sample of the supporting electrolyte solution having the supporting volume with a first addition volume of the electrodeposition solution thereby forming a first sample of the test mixture; and (B) contacting a second sample of the supporting electrolyte solution having the supporting volume with a second addition volume of the electrodeposition solution thereby forming a second sample of the test mixture; and optionally (C) repeating the step (B) up to n times, wherein n+2 corresponds to the number of samples in the plurality of samples of the test mixture.

In certain embodiments, the steps of providing a plurality of samples of a test mixture and measuring an electrodeposition rate for each sample of the test mixture comprise the steps of: (A) contacting a sample of the supporting electrolyte solution having the supporting volume with a first addition volume of the electrodeposition solution thereby forming a first sample of the test mixture, and measuring a first electrodeposition rate of the first sample of the test mixture; (B) adding a first extra volume of the electrodeposition solution into the first sample of the test mixture thereby forming a second sample of the test mixture, wherein a second addition volume of the electrodeposition solution used in preparing the second sample of the test mixture is the sum of the first addition volume of the electrodeposition solution and the first extra volume of the electrodeposition solution, and measuring a second electrodeposition rate of the second sample of the test mixture; and optionally (C) repeating step (B) up to n times, wherein n+2 corresponds to the number of samples in the plurality of samples of a test mixture In certain embodiments, the slope of the first linear relationship is determined at least by the steps of: providing a plurality of samples of the calibration mixture, wherein a concentration of the metal ion of each sample of the calibration mixture is known and the known concentrations of the metal ion of the plurality of samples of the calibration mixture are different; measuring an electrodeposition rate for each sample of the calibration mixture using the voltammetric measurement method; and calculating the slope of the first linear relationship based on the measured electrodeposition rates of the plurality of samples of the calibration mixture and the respective known concentrations of the metal ion of the plurality of samples of the calibration mixture.

In certain embodiments, each sample of the calibration mixture has a concentration of the metal ion between 0.01 g/L and 2 g/L.

In certain embodiments, each sample of the calibration mixture is prepared by contacting the supporting electrolyte solution at least with the metal ion, an acid, chloride ion, and one or more organic additives for electrodeposition.

In certain embodiments, each sample of the calibration mixture is prepared by contacting the supporting electrolyte solution with a calibration solution comprising the metal ion having a known concentration at a respective mixing ratio, and the respective mixing ratios used in preparing the plurality of samples of the calibration mixture are different.

In certain embodiments, the calibration solution comprises the same chemical components at substantially the same concentrations as the electrodeposition solution.

In certain embodiments, the known concentration of the metal ion of the calibration solution is between 0.08 mol/L and 1.2 mol/L.

In certain embodiments, a concentration ratio of the known concentration of the metal ion of the calibration solution to the known concentration of the metal ion of each sample of the calibration mixture is between 100:1 and 10000:1.

In certain embodiments, the step of providing a plurality of samples of the calibration mixture comprises the steps of: (A) providing a calibration solution comprising the same chemical components of the electrodeposition solution and having a known concentration of the metal ion; (B) contacting a first sample of the supporting electrolyte solution with a first addition volume of the calibration solution thereby forming a first sample of the calibration mixture; and (C) contacting a second sample of the supporting electrolyte solution with a second addition volume of the calibration solution thereby forming a second sample of the calibration mixture; and optionally (D) repeating the step (C) up to n times, wherein n+2 corresponds to the number of samples in the plurality of samples of the calibration mixture.

In certain embodiments, the steps of providing a plurality of samples of the calibration mixture and measuring an electrodeposition rate for each sample of the calibration mixture comprise the steps of: (A) providing a calibration solution comprising the same chemical components of the electrodeposition solution and having a known concentration of the metal ion; (B) contacting a sample of the supporting electrolyte solution with a first addition volume of the calibration solution thereby forming a first sample of the test mixture, and measuring a first electrodeposition rate of the first sample of the calibration mixture; (C) adding a first extra volume of the calibration solution into the first sample of the calibration mixture thereby forming a second sample of the calibration mixture, wherein a second addition volume of the calibration solution used in preparing the second sample of the calibration mixture is the sum of the first addition volume of the calibration solution and the first extra volume of the calibration solution, and measuring a second electrodeposition rate of the second sample of the calibration mixture; and optionally (D) repeating step (C) up to n times, wherein n+2 corresponds to the number of samples in the plurality of samples of a calibration mixture.

Provided herein is a method for optimizing the electrodeposition of a metal on a substrate comprising the steps of: depositing the metal on the substrate using a metal ion in an electrodeposition solution, wherein the metal ion is for forming the metal; during the step of depositing the metal on the substrate, measuring a concentration of the metal ion in the electrodeposition solution by the method described herein; and if the measured concentration of the metal ion is lower than a threshold concentration of the metal ion, adding an amount of the metal ion into the electrodeposition solution.

Provided herein is a system for performing the method for optimizing the electrodeposition of a metal on a substrate. The system comprises a voltammetric analyzer for measuring an electrodeposition rate of the electrodeposition solution; and a metal ion injection unit for adding an amount of the metal ion into the electrodeposition solution.

These and other aspects, features and advantages of the present disclosure will become more fully apparent from the following brief description of the drawings, the drawings, the detailed description of certain embodiments and appended claims.

BRIEF DESCRIPTION OF DRAWINGS

The appended drawings contain figures of certain embodiments to further illustrate and clarify the above and other aspects, advantages and features of the present invention. It will be appreciated that these drawings depict embodiments of the invention and are not intended to limit its scope. The invention will be described and explained with additional specificity and detail through the use of the accompanying drawings in which.

DETAILED DESCRIPTION OF THE INVENTION

The present disclosure relates to a method for measuring a concentration of a metal ion in an electrodeposition solution. The method of the present disclosure can substantially reduce the interference of organic additives and different electrode conditions on metal ion concentration measurements, thereby enabling to accurately measure metal ion concentrations in electrodeposition solutions using voltammetric measurement methods.

Figure 1:
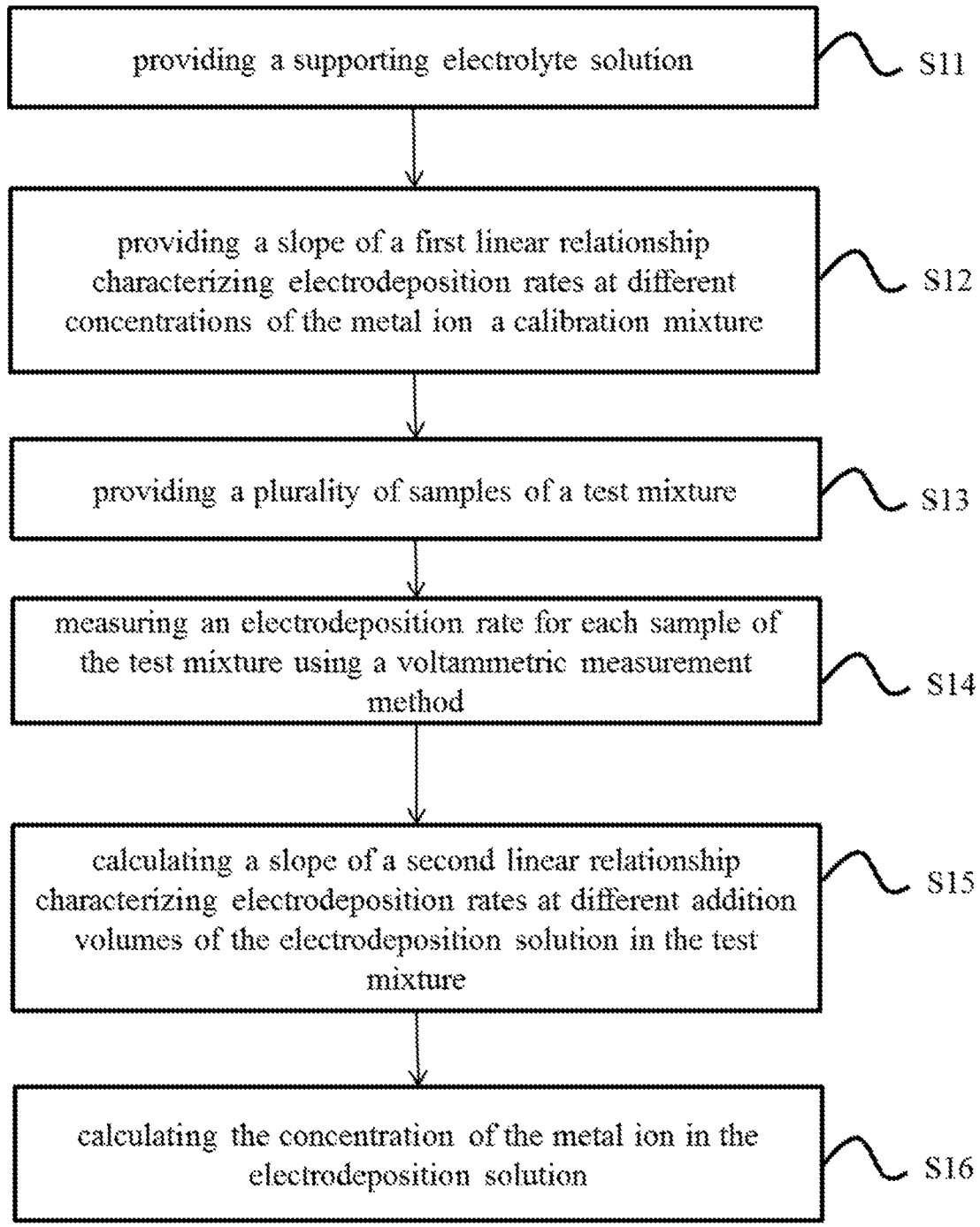
FIG. 1 shows a flow chart depicting a method for measuring a concentration of a metal ion in an electrodeposition solution according to certain embodiments.

FIG. 1 shows a flow chart depicting a method for measuring a concentration ($C_u$) of a metal ion in an electrodeposition solution according to certain embodiments. In step S11, a supporting electrolyte solution is provided. The supporting electrolyte solution is acidic and has a concentration of chloride ion less than 0.05 ppm. In step S12, a slope ($S_c$) of a first linear relationship is provided. The first linear relationship characterizes electrodeposition rates at different concentrations of the metal ion in a calibration mixture. In this embodiment, the slope of the first linear relationship is predetermined before the measurement. In step S13, a plurality of samples of a test mixture is provided. Each sample of the test mixture is prepared by contacting a supporting volume ($V_o$) of the supporting electrolyte solution with a respective addition volume of the electrodeposition solution, and the respective addition volumes of the electrodeposition solution used in preparing the plurality of samples of the test mixture are different. In step S14, an electrodeposition rate for each sample of the test mixture is measured using a voltammetric measurement method. In step S15, a slope ($S_s$) of a second linear relationship characterizing electrodeposition rates at different addition volumes of the electrodeposition solution in the test mixture is calculated based on the measured electrodeposition rates of the plurality of samples of the test mixture and the respective addition volumes of the electrodesposition solution. In step S16, the concentration of the metal ion in the electrodeposition solution is calculated by the following equation:

$$c_u = \frac{s_s}{s_c} \cdot V_0.$$

In certain embodiments, the electrodeposition solution comprises the metal ion, an acid, chloride ion, and one or more organic additives for electrodeposition.

In certain embodiments, the metal ion is copper ion, silver ion, nickel ion, zinc ion, or gold ion. The copper ion can be $Cu^{+2}$. The silver ion can be $Ag^{+1}$. The nickel ion can be $Ni^{+2}$. The zinc ion can be $Zn^{+2}$. The gold ion can be $Au^{+3}$. In certain embodiments, the acid is sulfuric acid, sulfonic acid, methanesulfonic acid, sulfamic acid, or citric acid.

In certain embodiments, the electrodeposition solution has a concentration of the chloride ion between 20 ppm and 100 ppm, between 40 ppm and 80 ppm, or 50 ppm and 70 ppm.

In certain embodiments, the one or more organic additives comprise an accelerator, a suppressor, a leveler or a combination thereof. The accelerator can be bis-(sodium sulfopropyl)-disulfide, 3-mercapto-propylsulfonic sodium salt, 3-mercapto-propylsulfonic acid-(3-sulfopropyl)ether, or 1-sodium-3-mercaptopropane-1-sulfonate. The suppressor can be polyethylene glycol 4000, polyethylene glycol 6000, or polyalkylene oxide random copolymer. The leveler can be 4-mercaptopyridine, 2-mercaptothiazoline, alkylated polyalkyleneimine, pyrrolidone, or imidazole.

In certain embodiments, the supporting electrolyte has a concentration of chloride ion less than 0.05 ppm, 0.005 ppm or 0.0005 ppm. The supporting electrolyte solution should be substantially free from chloride ion since the chloride ion, even in a slight amount, in the supporting electrolyte solution may substantially affect the accuracy of the metal ion concentration measurement.

In certain embodiments, the supporting electrolyte solution has a pH value less than 2 or less than 1. In certain embodiments, the supporting electrolyte solution has a pH of between −2 and 2; −1 and 2; 0 and 2; or 0 and 1. The supporting electrolyte solution having a high pH value can facilitate the electrodeposition of metal.

In certain embodiments, the supporting electrolyte solution comprises sulfate, alkylsulfonate, sulfamate, citrate, or a combination thereof.

As will be readily understood by a person skilled in the art, the actual chemical components present in the electrolyte solution can be affected by the pH of the electrolyte solution. For example, at very low pH at least a portion of the sulfate, alkylsulfonate, sulfamate, or citrate may exist in equilibrium with their conjugate acid. The proportion of the sulfate, alkylsulfonate, sulfamate, or citrate that exists as the conjugate acid at a given pH can readily be determined by a person skilled in the art. The alkylsulfonate can be a $C_1$-$C_{20}$ liner, branched or cyclic alkyl sulfonate. In certain embodiments, the alkylsulfonate is a $C_6$-$C_{10}$ liner or branched alkyl sulfonate. In certain embodiments, the alkylsulfonate is ethylhexyl sulfonate. In certain embodiments, the supporting electrolyte solution comprises a Group I alkali metal or Group II alkaline earth metal sulfate, alkylsulfonate, sulfamate, or citrate salt, or combinations thereof. In certain embodiments, the supporting electrolyte solution comprises a sodium sulfate, sodium alkylsulfonate, sodium sulfamate, or sodium citrate salt, or combinations thereof.

In certain embodiments, the supporting electrolyte solution has a concentration of any metal ions less than 0.01 g/L, 0.001 g/L or 0.0001 g/L. The supporting electrolyte solution should be substantially free from any metal ions since the metal ions, even in a slight amount, in the supporting electrolyte solution may substantially affect the accuracy of the metal ion concentration measurement.

In certain embodiments, each sample of the test mixture has a volume ratio of the supporting volume of the supporting electrolyte solution to the respective addition volume of the electrodeposition solution being between 100:1 and 10000:1, between 200:1 and 5000:1, or between 500:1 and 1500:1. If the volume ratio is lower than 100:1, the concentration of organic additives and chloride ion of such sample of the test mixture may be too high leading that the interference of the organic additives becomes dominant that may substantially reduce accuracy of the metal ion concentration measurement, and the second linear relationship for the test mixture may not be obtained. If the volume ratio is higher than 10000:1, the concentration of the metal ion of such sample of the test mixture may not be sufficient for measuring its electrodeposition rate.

In certain embodiments, the step of providing a plurality of samples of a test mixture comprises the steps of: (A) contacting a first sample of the supporting electrolyte solution having the supporting volume with a first addition volume of the electrodeposition solution thereby forming a first sample of the test mixture; and (B) contacting a second sample of the supporting electrolyte solution having the supporting volume with a second addition volume of the electrodeposition solution thereby forming a second sample of the test mixture; and optionally (C) repeating the step (B) up to n times, wherein n+2 corresponds to the number of samples in the plurality of samples of the test mixture.

In certain embodiments, the steps of providing a plurality of samples of a test mixture and measuring an electrodeposition rate for each sample of the test mixture comprise the steps of: (A) contacting a sample of the supporting electrolyte solution having the supporting volume with a first addition volume of the electrodeposition solution thereby forming a first sample of the test mixture, and measuring a first electrodeposition rate of the first sample of the test mixture; (B) adding a first extra volume of the electrodeposition solution into the first sample of the test mixture thereby forming a second sample of the test mixture, wherein a second addition volume of the electrodeposition solution used in preparing the second sample of the test mixture is the sum of the first addition volume of the electrodeposition solution and the first extra volume of the electrodeposition solution, and measuring a second electrodeposition rate of the second sample of the test mixture; and optionally (C) repeating step (B) up to n times, wherein n+2 corresponds to the number of samples in the plurality of samples of a test mixture.

In certain embodiments, the plurality of samples of the test mixture is between 2 and 20, 2 and 15, 2 and 10, and 5 and 10 samples of the test mixture.

In certain embodiments, the voltammetric measurement method for measuring an electrodeposition rate for each sample of the test mixture is a cyclic voltammetric scanning method, a cyclic pulse voltammetric scanning method, a chronoamperometric method, or a chronopotentiometric method.

In certain embodiments, the calibration mixture is configured such that the calibration mixture comprises the same chemical components as the test mixture. The concentrations of the chemical components between the calibration mixture and the test mixture can be in difference of below ±30%, ±20%, ±10%, ±5%, or ±1%.

In certain embodiments, the calibration mixture is configured such that the calibration mixture comprises the same chemical components at substantially the same concentration as the test mixture. If the calibration mixture is substantially similar to the test mixture, the slope of the first linear relationship for the test mixture can be determined in higher accuracy.

In certain embodiments, the slope of the second linear relationship for the test mixture is calculated using a linear regression analysis. In certain embodiments, firstly the slope the first liner relationship is determined, and secondly the slope the second liner relationship is determined. In certain embodiments, firstly the slope the second liner relationship is determined, and secondly the slope the first liner relationship is determined.

Figure 2:
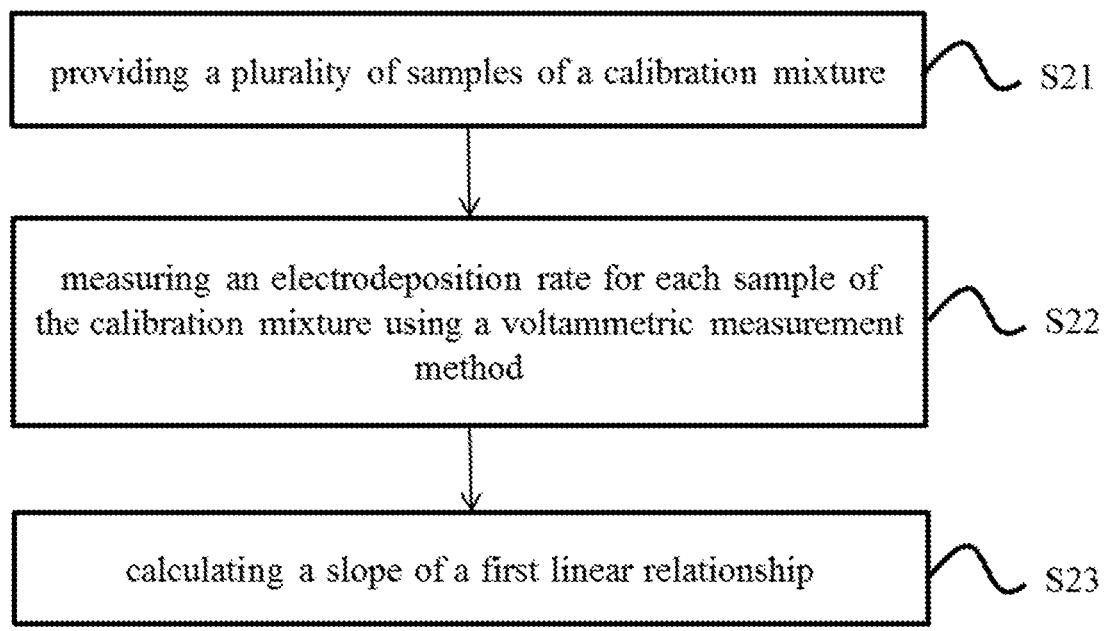
FIG. 2 shows a flow chart depicting a method for determining a slope of a first linear relationship characterizing electrodeposition rates at different concentrations of a metal ion in a calibration mixture according to certain embodiments.

FIG. 2 shows a flow chart depicting a method for determining a slope of a first linear relationship characterizing electrodeposition rates at different concentrations of a metal ion in a calibration mixture according to certain embodiments. In step S21, a plurality of samples of a calibration mixture is provided. A concentration of the metal ion of each sample of the calibration mixture is known and the known concentrations of the metal ion of the plurality of samples of the calibration mixture are different. In step S22, an electrodeposition rate for each sample of the calibration mixture is measured using a voltammetric measurement method. In step S23, a slope of the first linear relationship is calculated based on the measured electrodeposition rates of the plurality of samples of the calibration mixture and the respective known concentrations of the metal ion of the plurality of samples of the calibration mixture.

In certain embodiments, each sample of the calibration mixture has a concentration of the metal ion below between 0.01 g/L and 2 g/L, 0.1 g/L and 1.5 g/L, or 0.2 g/L and 1.2 g/L.

In certain embodiments, each sample of the calibration mixture is prepared by contacting the supporting electrolyte solution at least with the metal ion, an acid, chloride ion, and one or more organic additives for electrodeposition.

In certain embodiments, each sample of the calibration mixture is prepared by contacting the supporting electrolyte solution with a calibration solution having a known concentration of the metal ion at a respective mixing ratio, and the respective mixing ratios used in preparing the plurality of samples of the calibration mixture are different.

In certain embodiments, the calibration solution is configured such that the calibration solution comprises the same chemical components of the electrodeposition solution. The concentrations of the chemical components between the calibration solution and the electrodeposition can be in difference of below ±30%, ±20%, ±10%, ±5%, or ±1%.

In certain embodiments, the calibration solution is configured such that the calibration solution comprises the same chemical components at substantially the same concentrations as the electrodeposition solution.

In certain embodiments, the known concentration of the metal ion of the calibration solution is between 0.08 mol/L and 1.2 mol/L, 0.09 mol/L and 1.1 mol/L, or 0.095 mol/L and 1.05 mol/L.

In certain embodiments, a concentration ratio of the known concentration of the metal ion of the calibration solution to the known concentration of the metal ion of each sample of the calibration mixture is between 100:1 and 1000:1, between 200:1 and 5000:1, or between 500:1 and 1500:1. If the concentration ratio is lower than 100:1, the concentrations of organic additives and chloride ion of such sample of the calibration mixture may be too high leading that the interference of the organic additives becomes dominant that may substantially reduce accuracy of the metal ion concentration measurement, and the first linear relationship for the calibration mixture may not be obtained. If the volume ratio is higher than 10000:1, the concentration of the metal ion of such sample of the calibration mixture may not be sufficient for measuring its electrodeposition rates.

In certain embodiments, the step of providing a plurality of samples of the calibration mixture comprises the steps of: (A) providing a calibration solution comprising the same chemical components of the electrodeposition solution and having a known concentration of the metal ion; (B) contacting a first sample of the supporting electrolyte solution with a first addition volume of the calibration solution thereby forming a first sample of the calibration mixture; and (C) contacting a second sample of the supporting electrolyte solution with a second addition volume of the calibration solution thereby forming a second sample of the calibration mixture; and optionally (D) repeating the step (C) up to n times, wherein n+2 corresponds to the number of samples in the plurality of samples of the calibration mixture.

In certain embodiments, the steps of providing a plurality of samples of the calibration mixture and measuring an electrodeposition rate for each sample of the calibration mixture comprise the steps of: (A) providing a calibration solution comprising the same chemical components of the electrodeposition solution and having a known concentration of the metal ion; (B) contacting a sample of the supporting electrolyte solution with a first addition volume of the calibration solution thereby forming a first sample of the test mixture, and measuring a first electrodeposition rate of the first sample of the calibration mixture; (C) adding a first extra volume of the calibration solution into the first sample of the calibration mixture thereby forming a second sample of the calibration mixture, wherein a second addition volume of the calibration solution used in preparing the second sample of the calibration mixture is the sum of the first addition volume of the calibration solution and the first extra volume of the calibration solution, and measuring a second electrodeposition rate of the second sample of the calibration mixture; and optionally (D) repeating step (C) up to n times, wherein n+2 corresponds to the number of samples in the plurality of samples of a calibration mixture.

In certain embodiments, the plurality of samples of the calibration mixture is between 2 and 100 samples of the calibration mixture. In certain embodiments, the plurality of samples of the calibration mixture is between 2 and 20, 2 and 15, 2 and 10, and 5 and 10 samples of the calibration mixture.

In certain embodiments, the voltammetric measurement method for measuring an electrodeposition rate for each sample of the calibration mixture is a cyclic voltammetric scanning method, a cyclic pulse voltammetric scanning method, a chronoamperometric method, or a chronopotentiometric method.

In certain embodiments, the slope of the first linear relationship for the calibration mixture is calculated using a linear regression analysis.

For an electrodeposition solution comprising organic additives, a modified Bulter-Volmer Equation is developed for organic additive effects as follows:

$$i = i_0 \frac{C_{Cu^{2+}}^0}{C_{Cu^{2+}}^\infty}(1-\theta)\exp\left(-\frac{\alpha z F}{RT}\eta\right) \quad (1)$$

wherein i: current density on electrode, $i_o$: exchange current density, a: cathodic transfer coefficient, z: valence of metal ion, F: Faraday's constant, R: universal gas constant, T: absolute temperature, η: activation overpotential, $C_{Cu^{2+}}^\infty$: $Cu^{2+}$ concentration in the solution, $C_{Cu^{2+}}^0$: $Cu^{2+}$ concentration on electrode surface, and θ: surface coverage of organic additives on the deposited surface.

As shown in Equation (1), high surface coverage of organic additives on the deposited surface can substantially decrease the current density on electrode. It was surprising discovered that in the presence of chloride ion, the surface coverage of organic additives is more serious since one or more complexes comprising a metal ion, chloride ion and organic additives (e.g., a complex of polyethylene glycol (PEG)-$Cu^+$—$Cl^-$) are formed, which can adsorb on electrode/metal surface and substantially decrease the current density on electrode. In view of the above, it was surprisingly discovered that the interference of organic additive can be eliminated or minimized using the present method described herein.

The concentrations of organic additives and chloride ion in an electrodeposition solution can be substantially reduced by diluting the electrodeposition solution with an acidic supporting electrolyte solution, such that the formed complexes can be eliminated or substantially reduced. As the effect of organic additives is substantially reduced, θ will tend to become zero and the current density on electrode will be substantially proportional to $$\frac{C_{Cu^{2+}}^0}{C_{Cu^{2+}}^\infty}.$$

In view of the above, the following equation is developed:

$$\frac{\Delta c_u}{\Delta c_{cal}} = \frac{\Delta Q_u}{\Delta Q_{cal}} \quad (2)$$

wherein $\Delta c_u$: a change of the concentration of a metal ion in a test mixture, $\Delta c_{cal}$: a change of the concentration of the metal ion in a calibration mixture, $\Delta Q_u$: a change of the electrodeposition rate for the test mixture, and $\Delta Q_{cal}$: a change of the electrodeposition rate for the calibration mixture.

When $\Delta V_u$ is too small by comparing with $V_0$, $\Delta c_u$ is determined by the following equation:

$$\Delta c_u = \frac{\Delta V_u}{V_0} \cdot c_u \quad (3)$$

wherein $\Delta V_u$: an addition volume of a electrodeposition solution, $V_o$: a supporting volume of a supporting electrolyte solution, and $c_u$: a concentration of the electrodeposition solution.

By substituting Equation (3) into Equation (2), the following equation is provided:

$$c_u = \frac{\Delta Q_u/\Delta V_u}{\Delta Q_{cal}/\Delta C_{cal}} \cdot V_0 \quad (4)$$

In Equation (4), $\Delta Q_u/\Delta V_u$ is the slope ($S_s$) of the second linear relationship characterizing electrodeposition rates at different addition volumes of the electrodeposition solution in the test mixture, and $\Delta Q_{cal}/\Delta C_{cal}$ is the slope ($S_c$) of the first linear relationship characterizing electrodeposition rates at different concentrations of the metal ion in the calibration mixture. Thus, a concentration of a metal ion in an electrodeposition solution is calculated by the following equation:

$$c_u = \frac{S_s}{S_c} \cdot V_0 \quad (5)$$

Tests were conducted for showing the accuracy of metal ion concentration measurement by the present method described herein. Five samples of a calibration mixture were prepared by adding different additional volumes of a calibration solution into a supporting electrolyte solution. The calibration solution had 0.8 mol/L of $Cu^{2+}$, 100 g/L of sulfuric acid ($H_2SO_4$), 60 ppm of chloride ion, 1 ppm of bis-(sodium sulfopropyl)-disulfide (an accelerator), 200 ppm polyethylene glycol 4000 (a suppressor), 2 ppm alkylated polyalkyleneimine (a leveler). The supporting electrolyte solution was sulfuric acid having a concentration of 200 g/L. The electrodeposition rates of the samples of the calibration mixtures were measured by a voltammetric analyzer (CH Instruments with model number CHI600E) with rotating disk electrode at the operation mode of cyclic voltammetric stripping.

A first sample of the calibration mixture was prepared by adding a first addition volume of the calibration solution into the supporting electrolyte solution, and a first copper electrodeposition rate for the first sample was measured. A second sample of the calibration mixture was prepared by adding a first extra volume of the calibration solution into the first sample of the calibration mixture, wherein a second addition volume of the calibration solution used in preparing the second sample of the calibration mixture was the sum of the first addition volume of the calibration solution and the first extra volume of the calibration solution, and a second copper electrodeposition rate for the second sample of the calibration mixture was measured. The steps for preparing the second sample of the calibration mixture and measuring the second copper electrodeposition rate were repeated for third to fifth samples of the calibration mixture.

Figure 3:
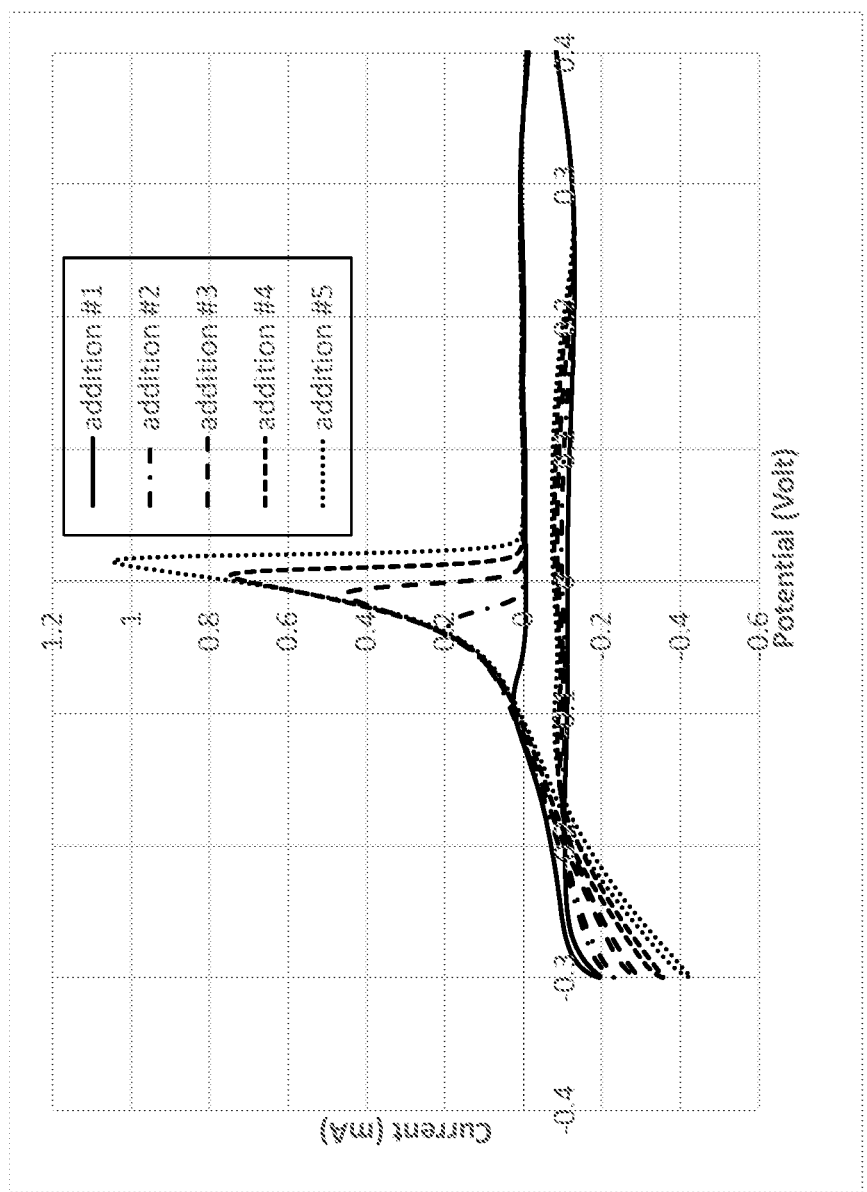
FIG. 3 shows a cyclic voltammogram for five samples of a calibration mixture according to certain embodiments.

FIG. 3 shows a cyclic voltammogram for the five samples of the calibration mixture. The cyclic voltammogram was obtained through the measurement results of the voltammetric analyzer. The area under each curve in the cyclic voltammogram is a copper electrodeposition rate for the respective sample of the calibration mixture.

Figure 4:
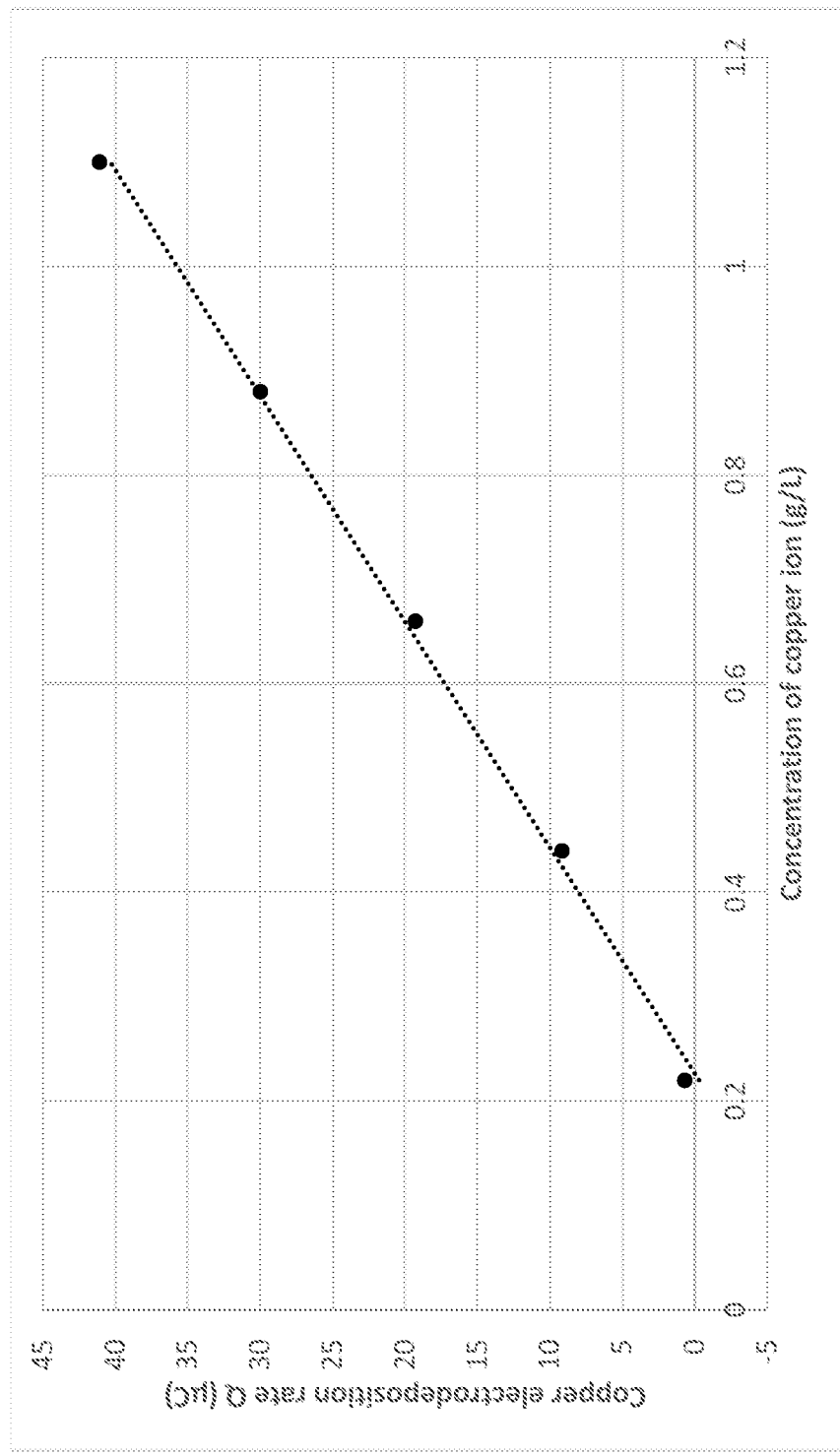
FIG. 4 shows a calibration plot of the copper electrodeposition rate as a function of the concentration of copper ion in the calibration mixture of FIG. 3.

FIG. 4 shows a calibration plot of the copper deposition rate as a function of the concentration of copper ion in the calibration mixture. The calibration plot was plotted based on the measured copper electrodeposition rates obtained in the cyclic voltammogram of FIG. 3 and their respective concentrations of copper ion in the samples of the calibration mixture. The slope of the calibration plot, being a slope of the first linear relationship, is calculated based on the measured copper electrodeposition rates and their respective concentrations of copper ion in the samples of the calibration mixture using a linear regression analysis. In this embodiment, the slope of the first linear relationship for the calibration mixture is 46.2 µCL/g.

Three electrodeposition solutions (including Electrodeposition solution 1, 2 and 3), having the same chemical components at the same concentrations as the calibration solution used in the calibration plot of FIG. 4 except that they contained 200 g/L (for Electrodeposition solution 1), 100 g/L (for Electrodeposition solution 2) and 50 g/L (for Electrodeposition solution 3) of copper ion, were prepared for forming three test mixtures including Test mixture 1, Test mixture 2 and Test mixture 3 respectively. The samples of each test mixture were prepared by adding different addition volumes of the corresponding electrodeposition solution into a supporting volume (30 mL) of the supporting electrolyte solution used in the calibration plot of FIG. 4. The copper electrodeposition rates of the samples of each test mixture were measured by the same voltammetric analyzer with rotating disk electrode at the operation mode of cyclic voltammetric stripping used in the calibration plot of FIG. 4.

A first sample of Test mixture 1 was prepared by adding a first addition volume of Electrodeposition solution 1 into 30 mL of the supporting electrolyte solution, and a first copper electrodeposition rate for the first sample of Test mixture 1 was measured. A second sample of Test mixture 1 was prepared by adding a first extra volume of the Electrodeposition solution 1 into the first sample of Test mixture 1, wherein a second addition volume of Electrodeposition solution 1 used in preparing the second sample of Test mixture 1 is the sum of the first addition volume of Electrodeposition solution 1 and the first extra volume of Electrodeposition solution 1, and a second electrodeposition rate of the second sample for Test mixture 1 was measured. The steps for preparing the second sample of Test mixture 1 and measuring the second copper electrodeposition rate were repeated for the remaining samples of Test mixture 1. Similar methods described above were used for preparing the samples of Test mixtures 2 and 3 and measuring their respective copper electrodeposition rates.

Figure 5:
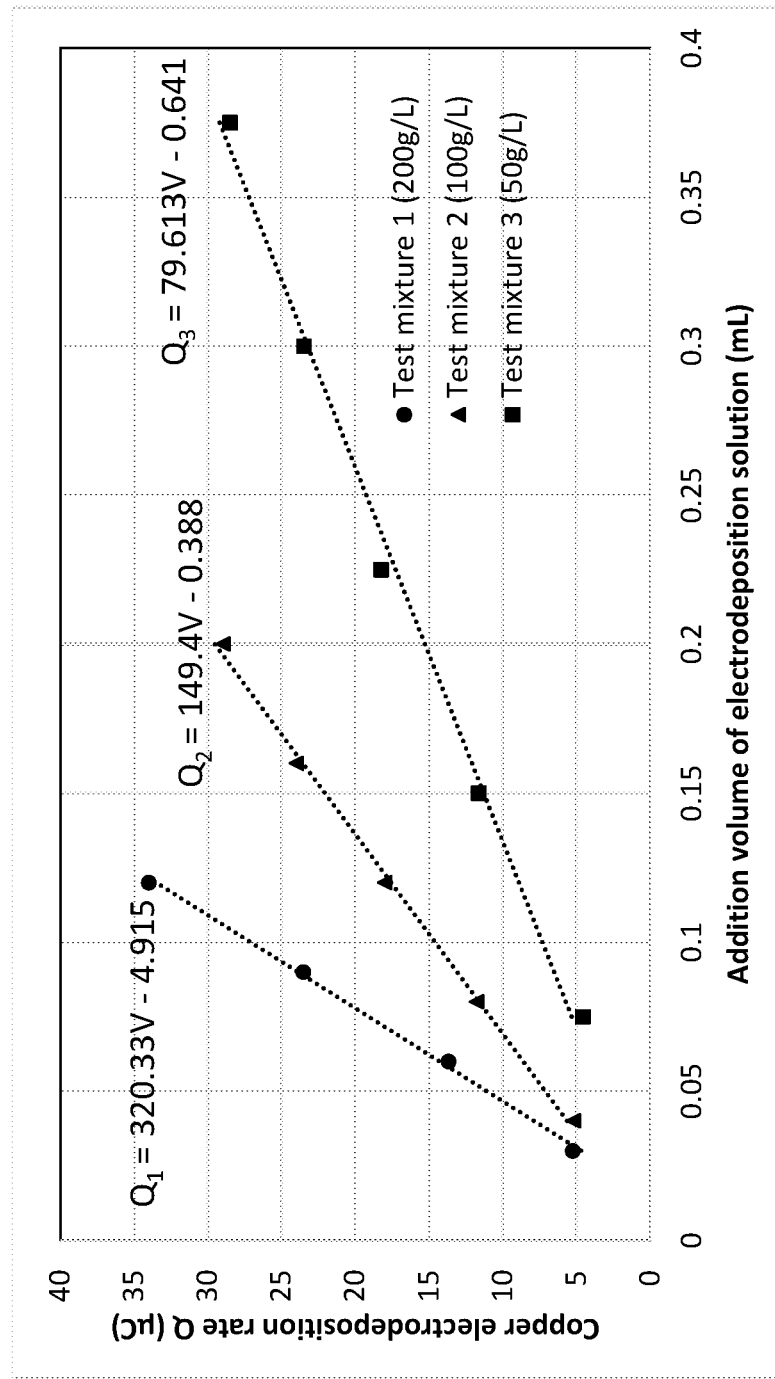
FIG. 5 shows three sample plots of the copper electrodeposition rate as a function of the addition volume of the electrodeposition solution in three test mixtures according to certain embodiments.

FIG. 5 shows three sample plots of the copper electrodeposition rate as a function of the addition volume of the corresponding electrodeposition solution in the three test mixtures. The sample plots were plotted based on the measured copper electrodeposition rates and their respective addition volumes of the corresponding electrodeposition solution. The slope of each sample plot, being a slope of the second linear relationship, is calculated based on the measured copper deposition rates and their respective addition volumes of the corresponding electrodeposition solution using the linear regression analysis. In these embodiments, the slopes of the second linear relationship for Test mixtures 1, 2 and 3 are 320.33 µC/mL, 149.4 µC/mL and 79.613 µC/mL respectively. The intercept values for Test mixtures 1, 2 and 3 are −4.915-0.338 µC and −0.641 µC respectively. Although Test mixtures 1, 2 and 3 came from substantially the same solution, the three intercept values are substantially different because of varied electrolyte temperatures and potential difference in condition of different electrodes.

Based on the calculated slopes of the calibration plot and the sample plots, the concentrations of copper ion in the three eletrodeposition solutions are calculated using Equation (5) by the present method described herein, and the calculated results are shown in Table 1.

TABLE 1

| Test mixture | Expected value (g/L) | Present method (g/L) | Error by present method (%) | Conventional method using intercept (g/L) | Error by conventional method (%) |
|---|---|---|---|---|---|
| 1 | 200 | 208.0 | 4% | 240.5 | 20.3% |
| 2 | 100 | 97.0 | −3% | 139.8 | 39.8% |
| 3 | 50 | 51.7 | 3.4% | 73.4 | 46.8% |

As shown in Table 1, the concentrations of copper ion measured by the present method are very close to the expected values, and the absolute errors generated by the present method are only between 3% and 4%. The above experimental results show that the present method can substantially reduce the interference of organic additives and different electrode conditions on metal ion concentration measurement, thus enabling to accurately measure metal ion concentrations in electrodeposition solutions using voltammetric measurement methods.

For comparison, a conventional method using the intercept of FIG. 4 is used to measure the concentrations of copper ion in the three electrodeposition solutions. For this conventional method, based on the measured fourth copper electrodeposition rate (shown in FIG. 5) for each test mixture, a concentration of copper ion for each test mixture is determined using the intercept of FIG. 4, and the determined concentration of copper ion is further multiplied by a ratio of the supporting volume to the corresponding addition volume of electrodeposition solution shown in FIG. 5. As shown in Table 1, the concentrations of copper ion calculated by the conventional method are far away from the expected values, and the absolute errors generated by this conventional method are between 20.3% and 46.8%. These errors are generated by varied electrolyte temperatures and different initial electrode conditions, which are evidenced by the three substantially different intercept values of the Test mixtures in FIG. 5. The above experimental results show that the data processing of the present method can eliminate the interference of varied electrolyte temperatures, background impurity ions in the supporting electrolyte solution and different initial conditions of electrodes.

Figure 6:
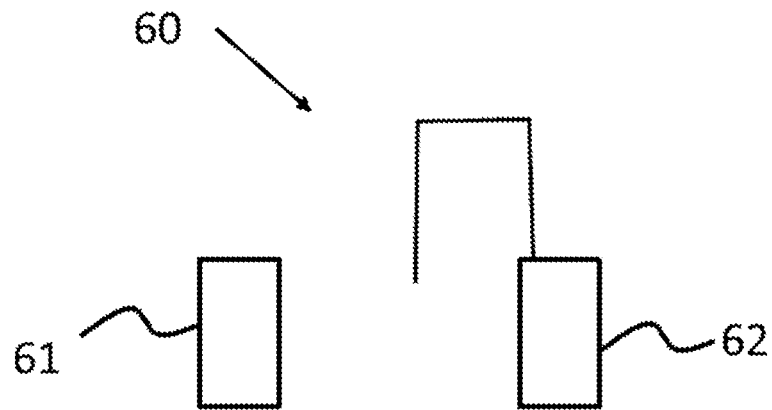
FIG. 6 depicts a system for optimizing the electrodeposition of a metal on a substrate according to certain embodiments.

FIG. 6 depicts a system for optimizing the electrodeposition of a metal on a substrate according to certain embodiments. The system 60 comprises a voltammetric analyzer 61 and a metal ion injection unit 62. The voltammetric analyzer 61 measures an electrodeposition rate of an electrodeposition solution. The metal ion injection unit 62 stores a metal ion and injects out an amount of the metal ion to control the concentration of the metal ion in the electrodesposition solution within a suitable range for optimizing the electrodesposition of the metal.

In certain embodiments, the voltammetric analyzer comprises a rotating disk electrode. The voltammetric analyzer with the rotating disk electrode can operate at the mode of cyclic voltammetric stripping for measuring an electrodeposition rate of an electrodeposition solution.

Figure 7:
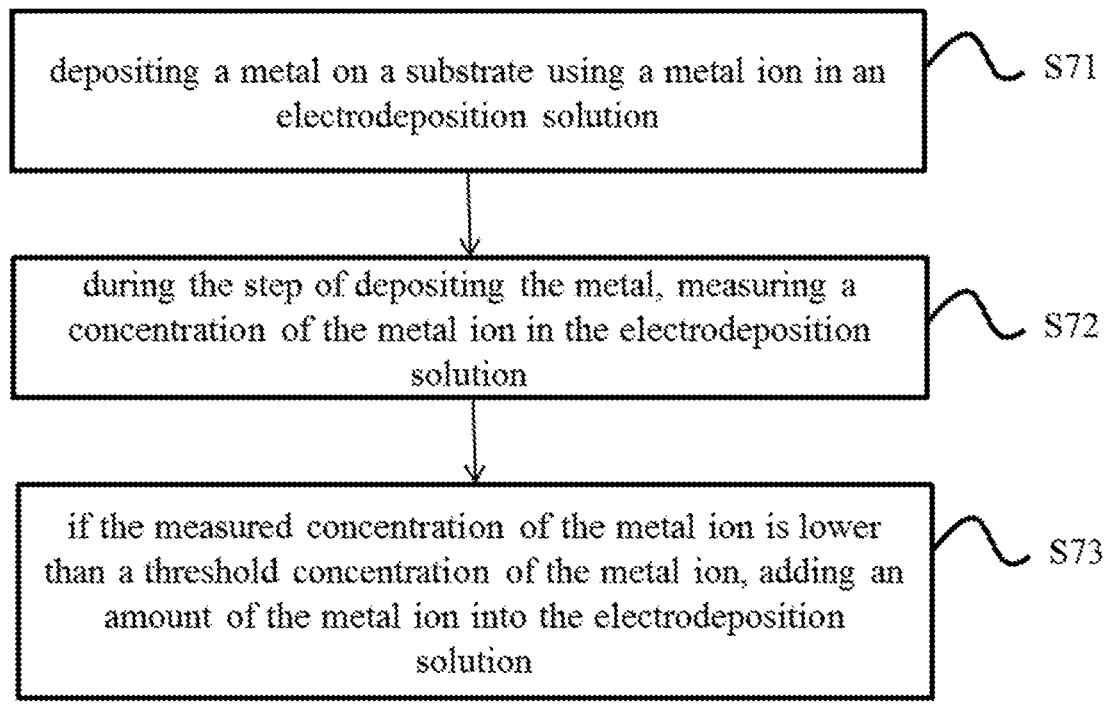
FIG. 7 shows a flow chart depicting a method for optimizing the electrodeposition of a metal on a substrate according to certain embodiments.

FIG. 7 shows a flow chart depicting a method for optimizing the electrodeposition of a metal on a substrate according to certain embodiments. In step S71, the metal is deposited on the substrate using a metal ion in an electrodeposition solution. In step S72, during the step of depositing the metal, a concentration of the metal ion in the electrodeposition solution is measured by the method described herein using a voltammetric analyzer. In step S73, if the measured concentration of the metal ion is lower than a threshold concentration of the metal ion, an amount of the metal ion is added to the electrodeposition solution using a metal ion injection unit.

In certain embodiments, the amount of the metal ion added to the electrodeposition solution is controlled to keep the concentration of the metal ion in the electrodeposition solution within a predetermined concentration range for optimizing the electrodeposition.

Provided herein a method for minimizing the interference of one or more organic additives during the measurement of a concentration of a metal ion in an electrodeposition solution comprising the steps of: providing a supporting electrolyte solution, wherein the supporting electrolyte solution is acidic and has a concentration of chloride ion less than 0.05 ppm; providing a slope ($S_c$) of a first linear relationship characterizing electrodeposition rates at different concentrations of the metal ion in a calibration mixture; providing a plurality of samples of a test mixture, wherein each sample of the test mixture is prepared by contacting a supporting volume ($V_o$) of the supporting electrolyte solution with a respective addition volume of the electrodeposition solution, and the respective addition volumes used in preparing the plurality of samples of the test mixture are different; measuring an electrodeposition rate for each sample of the test mixture using a voltammetric measurement method; calculating a slope ($S_s$) of a second linear relationship characterizing electrodeposition rates at different addition volumes of the electrodeposition solution in the test mixture based on the measured electrodeposition rates of the plurality of samples of the test mixture and the respective addition volumes of the plurality of samples of the test mixture; and calculating the concentration of the metal ion in the electrodeposition solution by the following equation:

$$c_u = \frac{S_s}{S_c} \cdot V_0.$$

In certain embodiments, the electrodeposition solution comprises the metal ion, an acid, chloride ion, and one or more organic additives for electrodeposition.

In certain embodiments, the electrodeposition solution has a concentration of the chloride ion between 20 ppm and 100 ppm.

In certain embodiments, the supporting electrolyte solution has a pH value less than 2.

In certain embodiments, each sample of the test mixture has a volume ratio of the supporting volume of the supporting electrolyte solution to the respective addition volume of the electrodeposition solution being between 100:1 and 10000:1.

In certain embodiments, the calibration mixture comprises the same chemical components of the test mixture.

In certain embodiments, the voltammetric measurement method is a cyclic voltammetric scanning method, a cyclic pulse voltammetric scanning method, a chronoamperometric method, or a chronopotentiometric method.

In certain embodiments, the step of providing a plurality of samples of a test mixture comprises the steps of: (A) contacting a first sample of the supporting electrolyte solution having the supporting volume with a first addition volume of the electrodeposition solution thereby forming a first sample of the test mixture; and (B) contacting a second sample of the supporting electrolyte solution having the supporting volume with a second addition volume of the electrodeposition solution thereby forming a second sample of the test mixture; and optionally (C) repeating the step (B) up to n times, wherein n+2 corresponds to the number of samples in the plurality of samples of the test mixture.

In certain embodiments, the steps of providing a plurality of samples of a test mixture and measuring an electrodeposition rate for each sample of the test mixture comprise the steps of: (A) contacting a sample of the supporting electrolyte solution having the supporting volume with a first addition volume of the electrodeposition solution thereby forming a first sample of the test mixture, and measuring a first electrodeposition rate of the first sample of the test mixture; (B) adding a first extra volume of the electrodeposition solution into the first sample of the test mixture thereby forming a second sample of the test mixture, wherein a second addition volume of the electrodeposition solution used in preparing the second sample of the test mixture is the sum of the first addition volume of the electrodeposition solution and the first extra volume of the electrodeposition solution, and measuring a second electrodeposition rate of the second sample of the test mixture; and optionally (C) repeating step (B) up to n times, wherein n+2 corresponds to the number of samples in the plurality of samples of a test mixture In certain embodiments, the slope of the first linear relationship is determined at least by the steps of: providing a plurality of samples of the calibration mixture, wherein a concentration of the metal ion of each sample of the calibration mixture is known and the known concentrations of the metal ion of the plurality of samples of the calibration mixture are different; measuring an electrodeposition rate for each sample of the calibration mixture using the voltammetric measurement method; and calculating the slope of the first linear relationship based on the measured electrodeposition rates of the plurality of samples of the calibration mixture and the respective known concentrations of the metal ion of the plurality of samples of the calibration mixture.

In certain embodiments, each sample of the calibration mixture has a concentration of the metal ion between 0.01 g/L and 2 g/L.

In certain embodiments, each sample of the calibration mixture is prepared by contacting the supporting electrolyte solution at least with the metal ion, an acid, chloride ion, and one or more organic additives for electrodeposition.

In certain embodiments, each sample of the calibration mixture is prepared by contacting the supporting electrolyte solution with a calibration solution comprising the metal ion having a known concentration at a respective mixing ratio, and the respective mixing ratios used in preparing the plurality of samples of the calibration mixture are different.

In certain embodiments, the calibration solution comprises the same chemical components at substantially the same concentrations as the electrodeposition solution.

In certain embodiments, the known concentration of the metal ion of the calibration solution is between 0.08 mol/L and 1.2 mol/L.

In certain embodiments, a concentration ratio of the known concentration of the metal ion of the calibration solution to the known concentration of the metal ion of each sample of the calibration mixture is between 100:1 and 10000:1.

In certain embodiments, the step of providing a plurality of samples of the calibration mixture comprises the steps of: (A) providing a calibration solution comprising the same chemical components of the electrodeposition solution and having a known concentration of the metal ion; (B) contacting a first sample of the supporting electrolyte solution with a first addition volume of the calibration solution thereby forming a first sample of the calibration mixture; and (C) contacting a second sample of the supporting electrolyte solution with a second addition volume of the calibration solution thereby forming a second sample of the calibration mixture; and optionally (D) repeating the step (C) up to n times, wherein n+2 corresponds to the number of samples in the plurality of samples of the calibration mixture.

In certain embodiments, the steps of providing a plurality of samples of the calibration mixture and measuring an electrodeposition rate for each sample of the calibration mixture comprise the steps of: (A) providing a calibration solution comprising the same chemical components of the electrodeposition solution and having a known concentration of the metal ion; (B) contacting a sample of the supporting electrolyte solution with a first addition volume of the calibration solution thereby forming a first sample of the test mixture, and measuring a first electrodeposition rate of the first sample of the calibration mixture; (C) adding a first extra volume of the calibration solution into the first sample of the calibration mixture thereby forming a second sample of the calibration mixture, wherein a second addition volume of the calibration solution used in preparing the second sample of the calibration mixture is the sum of the first addition volume of the calibration solution and the first extra volume of the calibration solution, and measuring a second electrodeposition rate of the second sample of the calibration mixture; and optionally (D) repeating step (C) up to n times, wherein n+2 corresponds to the number of samples in the plurality of samples of a calibration mixture.

Although the invention has been described in terms of certain embodiments, other embodiments apparent to those of ordinary skill in the art are also within the scope of this invention. Accordingly, the scope of the invention is intended to be defined only by the claims which follow.

What is claimed is:

1. A method for measuring a concentration ($C_u$) of a metal ion in an electrodeposition solution comprising the steps of:

providing a supporting electrolyte solution, wherein the supporting electrolyte solution is acidic and has a concentration of chloride ion less than 0.05 ppm and a concentration of any metal ions less than 0.01 g/L;

providing a slope ($S_c$) of a first linear relationship characterizing electrodeposition rates at different concentrations of the metal ion in a calibration mixture;

providing a plurality of samples of a test mixture, wherein each sample of the test mixture is prepared by contacting a first volume ($V_o$) of the supporting electrolyte solution with a respective addition volume of the electrodeposition solution, and the respective addition volumes of the electrodeposition solution used in preparing the plurality of samples of the test mixture are different;

measuring an electrodeposition rate for each sample of the test mixture using a voltammetric measurement method;

calculating a slope ($S_s$) of a second linear relationship characterizing electrodeposition rates at different addition volumes of the electrodeposition solution in the test mixture based on the measured electrodeposition rates of the plurality of samples of the test mixture and the respective addition volumes of the electrodeposition solution; and calculating the concentration of the metal ion in the electrodeposition solution by the following equation:

$$c_u = \frac{s_s}{s_c} \cdot V_0.$$

2. The method of claim 1, wherein the electrodeposition solution comprises the metal ion, an acid, chloride ion, and one or more organic additives for electrodeposition.

3. The method of claim 2, wherein the electrodeposition solution has a concentration of the chloride ion between 20 ppm and 100 ppm.

4. The method of claim 1, wherein the supporting electrolyte solution has a pH value less than 2.

5. The method of claim 1, wherein each sample of the test mixture has a volume ratio of the first volume of the supporting electrolyte solution to the respective addition volume of the electrodeposition solution being between 100:1 and 10000:1.

6. The method of claim 1, wherein the calibration mixture comprises the same chemical components of the test mixture.

7. The method of claim 1, wherein the voltammetric measurement method is a cyclic voltammetric scanning method, a cyclic pulse voltammetric scanning method, a chronoamperometric method, or a chronopotentiometric method.

8. The method of claim 1, wherein the step of providing a plurality of samples of a test mixture comprises the steps of:

(A) contacting a first sample of the supporting electrolyte solution having the first volume with a first addition volume of the electrodeposition solution thereby forming a first sample of the test mixture; and (B) contacting a second sample of the supporting electrolyte solution having the first volume with a second addition volume of the electrodeposition solution thereby forming a second sample of the test mixture; and optionally (C) repeating the step (B) up to n times, wherein n+2 corresponds to the number of samples in the plurality of samples of the test mixture.

9. The method of claim 1, wherein the steps of providing a plurality of samples of a test mixture and measuring an electrodeposition rate for each sample of the test mixture comprise the steps of:

(A) contacting a sample of the supporting electrolyte solution having the first volume with a first addition volume of the electrodeposition solution thereby forming a first sample of the test mixture, and measuring a first electrodeposition rate of the first sample of the test mixture;

(B) adding a first extra volume of the electrodeposition solution into the first sample of the test mixture thereby forming a second sample of the test mixture, wherein a second addition volume of the electrodeposition solution used in preparing the second sample of the test mixture is the sum of the first addition volume of the electrodeposition solution and the first extra volume of the electrodeposition solution, and measuring a second electrodeposition rate of the second sample of the test mixture; and optionally (C) repeating step (B) up to n times, wherein n+2 corresponds to the number of samples in the plurality of samples of a test mixture.

10. The method of claim 1, wherein the slope of the first linear relationship is determined at least by the steps of:

providing a plurality of samples of the calibration mixture, wherein a concentration of the metal ion of each sample of the calibration mixture is known and the known concentrations of the metal ion of the plurality of samples of the calibration mixture are different;

measuring an electrodeposition rate for each sample of the calibration mixture using the voltammetric measurement method; and calculating the slope of the first linear relationship based on the measured electrodeposition rates of the plurality of samples of the calibration mixture and the respective known concentrations of the metal ion of the plurality of samples of the calibration mixture.

11. The method of claim 10, wherein each sample of the calibration mixture has a concentration of the metal ion between 0.01 g/L and 2 g/L.

12. The method of claim 10, wherein each sample of the calibration mixture is prepared by contacting the supporting electrolyte solution at least with the metal ion, an acid, chloride ion, and one or more organic additives for electrodeposition.

13. The method of claim 10, wherein each sample of the calibration mixture is prepared by contacting the supporting electrolyte solution with a calibration solution having a known concentration of the metal ion at a respective mixing ratio, and the respective mixing ratios used in preparing the plurality of samples of the calibration mixture are different.

14. The method of claim 13, wherein the calibration solution comprises the same chemical components at substantially the same concentrations as the electrodeposition solution.

15. The method of claim 13, wherein the known concentration of the metal ion of the calibration solution is between 0.08 mol/L and 1.2 mol/L.

16. The method of claim 13, wherein a concentration ratio of the known concentration of the metal ion of the calibration solution to the known concentration of the metal ion of each sample of the calibration mixture is between 100:1 and 10000:1.

17. The method of claim 10, wherein the step of providing a plurality of samples of the calibration mixture comprises the steps of:

(A) providing a calibration solution comprising the same chemical components of the electrodeposition solution and having a known concentration of the metal ion;

(B) contacting a first sample of the supporting electrolyte solution with a first addition volume of the calibration solution thereby forming a first sample of the calibration mixture; and (C) contacting a second sample of the supporting electrolyte solution with a second addition volume of the calibration solution thereby forming a second sample of the calibration mixture; and optionally (D) repeating the step (C) up to n times, wherein n+2 corresponds to the number of samples in the plurality of samples of the calibration mixture.

18. The method of claim 10, wherein the steps of providing a plurality of samples of the calibration mixture and measuring an electrodeposition rate for each sample of the calibration mixture comprise the steps of:

(A) providing a calibration solution comprising the same chemical components of the electrodeposition solution and having a known concentration of the metal ion;

(B) contacting a sample of the supporting electrolyte solution with a first addition volume of the calibration solution thereby forming a first sample of the test mixture, and measuring a first electrodeposition rate of the first sample of the calibration mixture;

(C) adding a first extra volume of the calibration solution into the first sample of the calibration mixture thereby forming a second sample of the calibration mixture, wherein a second addition volume of the calibration solution used in preparing the second sample of the calibration mixture is the sum of the first addition volume of the calibration solution and the first extra volume of the calibration solution, and measuring a second electrodeposition rate of the second sample of the calibration mixture; and optionally (D) repeating step (C) up to n times, wherein n+2 corresponds to the number of samples in the plurality of samples of a calibration mixture.

19. A method for optimizing the electrodeposition of a metal on a substrate comprising the steps of:

depositing the metal on the substrate using a metal ion in an electrodeposition solution, wherein the metal ion is for forming the metal;

during the step of depositing the metal on the substrate, measuring a concentration of the metal ion in the electrodeposition solution by the method of claim 1; and if the measured concentration of the metal ion is lower than a threshold concentration of the metal ion, adding an amount of the metal ion into the electrodeposition solution.

20. A system for performing the method of claim 19 comprising:

a voltammetric analyzer for measuring an electrodeposition rate of the electrodeposition solution.

* * * * *